United States Patent [19]

Bose et al.

[11] Patent Number: 5,311,598
[45] Date of Patent: May 10, 1994

[54] METHOD AND APPARATUS FOR SURFACE INSPECTION

[75] Inventors: Chinmoy B. Bose, Green Brook; Rajarshi Ray, Princeton, both of N.J.

[73] Assignee: AT&T Bell Laboratories, Murray Hill, N.J.

[21] Appl. No.: 537,846

[22] Filed: Jun. 13, 1990

Related U.S. Application Data

[63] Continuation of Ser. No. 259,640, Oct. 18, 1988, Pat. No. 4,975,972.

[51] Int. Cl.⁵ ............................................. G06K 9/00
[52] U.S. Cl. ................................. 382/8; 382/1; 382/51; 382/49; 348/126; 348/128
[58] Field of Search ................. 382/1, 8, 51, 55, 49, 382/27; 356/237; 358/106, 461, 465

[56] References Cited

U.S. PATENT DOCUMENTS 4,601,057  7/1986  Tsugi et al. ........................ 382/51
4,700,225  10/1987  Hara et al. ........................ 358/106

OTHER PUBLICATIONS

Yoda et al, An Automatic Wafer Inspection Using Pipelined Image Processing Techniques, Jan. 198, 4–16.

*Primary Examiner*—David K. Moore
*Attorney, Agent, or Firm*—Robert B. Levy

[57] ABSTRACT

Detection of a defect (18) on the surface (15) of an article (10), such as a semiconductor chip, is accomplished by illuminating the chip in a bright field and then capturing the image thereof with a television camera (30) coupled to a machine vision processor (32). To detect the defect (18), the vision processor first adaptively thresholds the captured image to effectively eliminate areas in the image brighter than those associated with the defect (18) which are usually dark. Thereafter, the vision processor (32) erodes and then dilates the dark areas within the image remaining after binarization to isolate those dark areas associated with the defect. The existence of a defect can then be established by the existence of a now-isolated dark area.

1 Claim, 4 Drawing Sheets

METHOD AND APPARATUS FOR SURFACE INSPECTION

This is a continuation of U.S. application Ser. No. 259,640 filed Oct. 18, 1988, now U.S. Pat. No. 4,975,972.

TECHNICAL FIELD

This invention relates to a method and apparatus for inspecting a surface on a substrate to detect defects, if any, thereon.

BACKGROUND OF THE INVENTION

There are many articles, such as semiconductors chips for example, which, during manufacture, become damaged and are either immediately rendered inoperative or have their operating lifetime reduced when their exposed surface(s) becomes scratched or stained. Thus, during the manufacture of such articles, one or more visual inspections are commonly performed to detect any surface defects, so that articles bearing a defect can be repaired, if possible, or if not, they can be scrapped prior to any subsequent processing. Detection of defects at an early stage of manufacture helps to reduce manufacturing costs and improve manufacturing yields.

Visual detection of surface defects is a relatively easy task when the article has relatively large surface features. Detection of defects becomes more difficult when the surface features are small, as in the case of a semiconductor chip having an exposed surface whose features have a linewidth often no larger than several microns. The small linewidth of the features on the exposed surface of the semiconductor chip has heretofore made it impractical to employ present day automated vision equipment to detect defects on the exposed chip surface. This is because most automated vision equipment accomplishes inspection by the technique of "pattern matching," which involves matching the image of the article undergoing inspection to that of a perfect or "golden" pattern.

The process of detecting defects by the technique of pattern matching requires that the image of the pattern on the article undergoing inspection be accurately registered with the golden pattern. Otherwise, a match between the pattern on the article and the golden pattern becomes practically impossible to obtain. Registration of the pattern of the exposed surface on each of a plurality of chips, formed on a wafer, with a golden pattern, representing a set of perfectly formed chip features, is possible because one or more fiducials are usually present on the wafer. However, once the wafer is diced to separate the chips, it is difficult to register the pattern on each chip with the golden pattern because of the extremely small size of the features and the absence of any fiducials on the chip.

There is a need for a technique for visually detecting very small surface defects, such as scratches or stains, on a semiconductor chip, because often, such defects do not manifest themselves during electrical testing of the chip. As a result, when a semiconductor chip bearing a stain or crack is packaged to form an integrated circuit, there is the likelihood that the integrated circuit may prematurely fail in the field as a result of vibration and thermal cycling.

SUMMARY OF THE INVENTION

Briefly, in accordance with a preferred embodiment of the invention, a technique is provided for automated inspection of at least one surface of an article, such as a semiconductor chip, to detect defects, such as stains and scratches, which, when illuminated, tend to appear dark. Initially, the chip is illuminated by directing light at the surface of the chip so that the light strikes the surface substantially normal to the plane thereof in order to maximize any scattering of the light by the defects, if any, on the surface. Thereafter, the image of the surface of the chip is captured by an image-acquisition device whose optical axis is substantially normal to the plane of the surface of the chip. The captured image is then adaptively binarized, typically, by assigning a first intensity value (usually zero) to these areas within the image whose actual intensity value is less than a particular threshold value, which in practice, is set in accordance with a histogram of the image intensity. Those areas in the image whose intensity value is above the threshold are assigned a second intensity value, typically much greater than zero. As a result of binarization, the image of the surface now contains only dark (i.e., black) and very bright (i.e., white) areas.

After the image of the surface of the chip has been binarized, the image is further processed to isolate each dark area which is associated with a non-reflective defect (if any), such as a scratch or stain, present on the surface of the chip. In a preferred embodiment, the image is processed, following binarization, by repeatedly eroding all of the dark areas within the image of the chip until the only the dark area associated with each defect remains. Thereafter, the remaining dark areas, each associated with a defect, are then repeatedly dilated the same number of times the dark areas were previously eroded. The number of erosions and dilations is dependent on the size (linewidth) of those dark areas associated with features normally present on the surface of the chip. The presence of a dark area remaining in the image of the chip after the erosion and dilation operations signifies the existence of a defect on the surface of the chip.

As may now be appreciated, the present defect detection method operates without resort to any pattern matching.

BRIEF DESCRIPTION OF THE DRAWING

FIG. 9 is a flowchart representation of a program executed by the apparatus of FIG. 1 to detect defects on the semiconductor chip which are both smaller and larger than the linewidth of the features on the chip.

DETAILED DESCRIPTION

Figure 1:
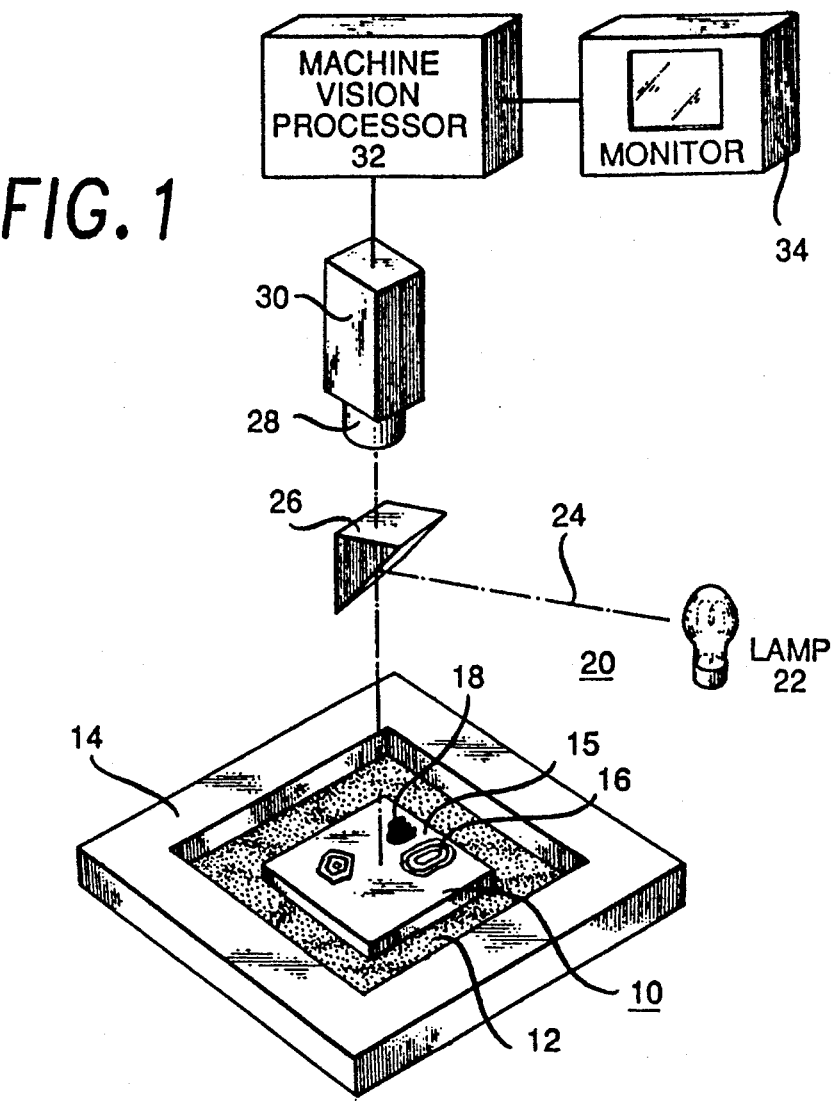
FIG. 1 is a block diagram of an apparatus, in accordance with a preferred embodiment of the present invention, for inspecting a semiconductor chip to detect defects, if any, on its exposed surface.

FIG. 1 is a perspective view of a semiconductor chip 10, which is surrounded by, and which overlies a portion of, a volume of bonding material 12 that secures the chip within a recess in a chip carrier 14 such that the chip has its major surface 15 exposed. In the process of bonding the chip 10 to the chip carrier 14, it is not unusual for the exposed surface 15, which has a plurality of very fine features 16 thereon, to become scratched or stained, giving rise to one or more surface defects 18, only one of which is shown. When the defect 18 is as large as or larger than the linewidth of the features 16 (which is usually on the order 1-5 microns), the defect may cause damage to the features, possibly rendering the chip 10 defective by causing it to be inoperative or have a much reduced lifetime.

In FIG. 1 there is shown an apparatus 20, in accordance with a preferred embodiment of the invention, for detecting the defect 18 on the surface 15 of the semiconductor chip 10. The apparatus 20 includes a light source 22, such as a tungsten-halogen lamp or the like, which produces a beam or light 24 that is directed into a beam splitter 26. The beam splitter 26, which is conventional in its construction, directs the beam 24 towards the chip 10 so that the beam strikes the surface 15 normal to the plane thereof. In addition, the beam splitter 24 also serves to direct those portions of the beam 24, which are reflected normally from the surface 15, into lens 28 mounted on an image-acquisition device 30, typically taking the form of a television camera whose optical axes is substantially normal to the surface.

The technique of illuminating the chip 10 by directing the beam 24 at the surface 15 normal to the plane of the surface and then sensing the intensity of the light reflected normal to the plane thereof is known as "bright field illumination." In contrast, the technique of directing the beam 24 towards the surface 15 at an acute angle with respect to the plane thereof and then sensing the intensity of the light reflected from the surface normal to the plane thereof is referred to as "dark field illumination." Bright field illumination is preferable because the image of the surface 15 captured by the television camera 30 will be brighter than under dark field illumination.

Under bright field illumination, the intensity of the light expected to be reflected into the lens 28 on the camera 30 from the area on the surface 15 occupied by the defect 18 will equal a small portion of the total light scattered by the defect area. The area on the surface 15 surrounding each defect 18 tends to reflect substantially all of the beam 24 incident thereon into the lens 28. Therefore, the presence of each defect 18 can be detected by a large reduction in the light received by the camera 30 from each area on the surface 15 occupied by the associated defect.

Under dark field illumination, the intensity of the light expected to be reflected into the lens 28 from each area occupied by a defect 18 will also equal a small portion of the total light scattered from the associated defect area. However, under dark field illumination, the area surrounding each defect 18 is not expected to reflect light into the lens 28. Therefore, the presence of a defect 18 will not cause a significant change in the intensity of the light reflected into the lens 28 on the camera 30 from each defect area, as compared to those areas on the surface 15 not occupied by a defect. Hence, bright field illumination provides a more efficient technique for detecting each defect 18, such as a scratch or stain, on the surface 15.

The inspection apparatus 20 further includes a machine vision processor 32 coupled to the television camera 30 for processing its output signal, typically an analog voltage that varies in accordance with the intensity of the image captured by the camera. In practice, the vision processor 32 takes the form of a commercial vision system, such as the model P256 vision system manufactured by IRI Copr., Carlsbad, Calif. The vision processor 32 is coupled to a monitor 34 so that the output of the vision processor can be displayed.

Figure 2:
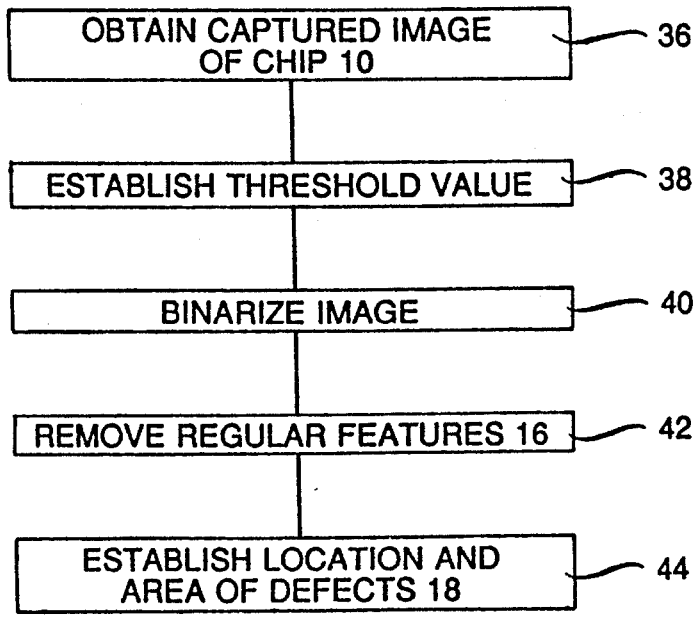
FIG. 2 is a flowchart representation of a program executed by the apparatus of FIG. 1 to inspect the semiconductor chip.

The operation of the apparatus 20 may best be understood by reference to FIG. 2, which shows a flowchart representation of a computer program executed by the vision processor 32 to detect each defect 18 (if any) on the surface 15 (all of FIG. 1). Referring to FIG. 2, upon execution of the program, the vision processor 32 of FIG. 1 initially executes step 36 of FIG. 2 and obtains the image of the surface 15 of the chip 10 captured by the camera 30, both of FIG. 1. To obtain the image of the surface 15, the vision processor 32 converts the analog output signal of the camera 30 into a stream of digital signals, each representing the intensity of a separate small area (pixel) within the image. The digital signal representing the intensity of each pixel is typically eight bits in length, so the intensity (as measured in shades of gray) of each pixel ranges in value between 0 (black) and 255 (white).

Referring to FIG. 1, the vision processor 32 typically converts the output signal of the television camera 30 into 61,440 digital signals, each representing the intensity of a separate one of the pixels within a $240 \times 256$ pixel array comprising the image of the surface 15 captured by the camera. In practice, the optical properties of the lens 28 on the camera 30 are selected such that each of the pixels within the $240 \times 256$ array corresponds to a 5 $\mu m \times 5$ $\eta m$ area on the surface 15. It should be understood that the particular size of the pixel array is dependent on the characteristics of the vision processor 32 and that larger arrays are possible. Further, the physical size of each pixel within the array is dependent on the optical properties on the lens 28.

Figure 3:
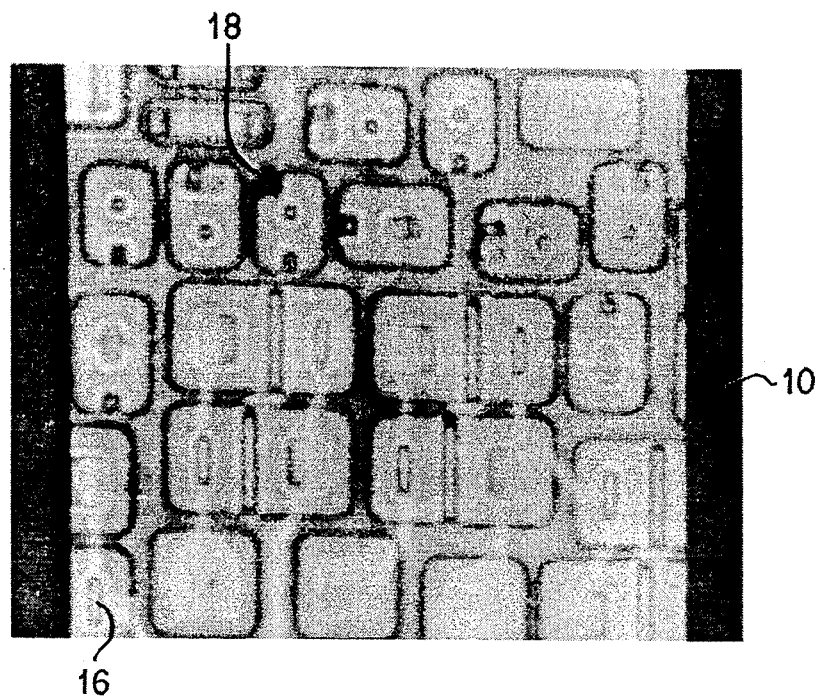
FIG. 3 shows the image of the chip captured by the apparatus of FIG. 1 during execution of the program of FIG. 2.

Referring now to FIG. 3, there is shown the image of the surface 15 of the chip 10 of FIG. 1 established by the vision processor 32 of FIG. 1 during step 36 of FIG. 2. As can be observed in FIG. 3, the defect 18 is represented by a dark spot appearing near the upper left-hand corner of the image. Detection of the defect 18 would be a relatively easy task if there were no other dark areas within the image of FIG. 3. However, on the surface 15 of FIG. 1 there are regularly occurring features 16 of varying gray levels, including individual cell walls, known as "tubs," which appear in FIG. 3 as black squares and rectangles.

In order to detect the defect 18, it is necessary to isolate those regularly occurring features 16 from each area with a defect 18. To facilitate isolation of the defect 18, it is useful to binarize or threshold the image of FIG. 3 so that those features 16 which are brighter (i.e., they have a higher pixel intensity or gray level) than the defect are made to appear white. As will be described below, the image of FIG. 3 is binarized by setting t zero the intensity (gray level) of those pixels in the image whose true intensity is below a threshold value t so that pixels now appear black. Those pixels within the image of the surface 15 whose true intensity is higher than the threshold value t are assigned an intensity value of 255 so the pixels now appear white.

Figure 4:
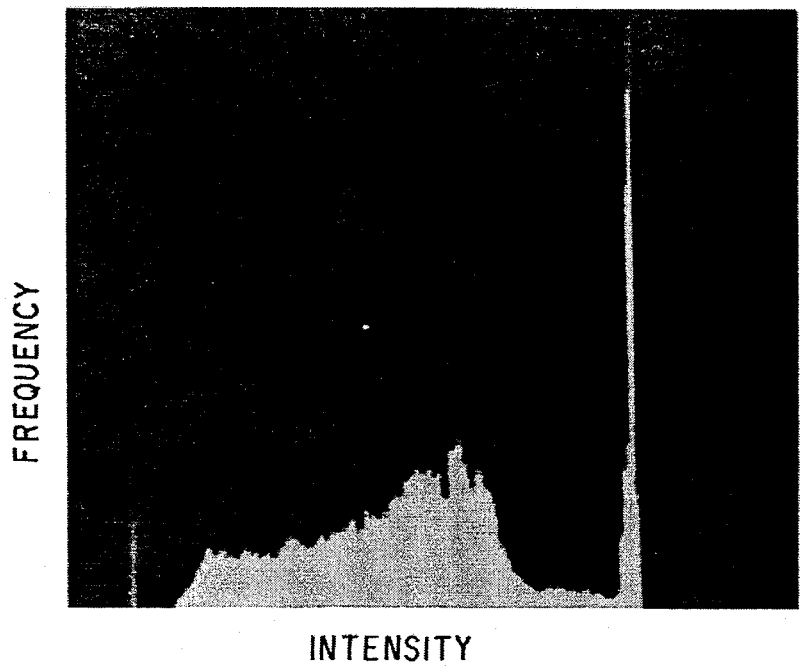
FIG. 4 shows a histogram of the intensities of the pixels within the image of FIG. 3.

Before the image shown in FIG. 3 can be binarized, the threshold value t must be set. Referring to FIG. 2, following step 36, the vision processor 32 of FIG. 1 adaptively sets the threshold value t during sep 38. In practice, the vision processor 32 adaptively sets the threshold value t during step 38 of FIG. 2 in accordance with the pixel intensity frequency, that is, the number of pixels within the image of FIG. 3 that have a particular intensity level. A plot of the pixel intensity frequency, often referred to as a histogram, is shown in FIG. 4.

There are several techniques by which the vision processor 32 of FIG. 1 can adaptively set the threshold value t in accordance with the pixel intensity frequency. For example, the threshold value t can be set equal to the means of the intensity of the pixels in the image of FIG. 3 less the product of $k_1$ and the pixel intensity variance, where $k_1$ is a constant. The pixel intensity means and variance are established by the vision processor 32 of FIG. 1 from the pixel histogram shown in FIG. 4. Another approach is to set the threshold value t equal to the product of $k_2$ and the means of the intensity of the pixels, where $k_2$ is a constant less than unity. Both of these approaches, which depend on the mean of dependent of the type of semiconductor chip 10 undergoing inspection.

Yet another approach to establishing the threshold value t is to set the value equal the product of $k_3$, where $k_3$ is a constant less than unit, and the pixel intensity at a point just below the first non-zero peak or knee of the histogram of FIG. 4 where the left-side slope is greater than the right-side slope. The pixel intensity at the point just below the first non-zero histogram peak has been found to be just above the intensity of those pixels within the image of FIG. 3 corresponding to the defect 18. Establishing the threshold value t in the manner just described has been found to be independent of the type of chip 10 undergoing inspection and is the preferable approach. However, it should be noted that this approach tends to be somewhat more sensitive to variations in the illumination of the surface 15 of the chip 10 of FIG. 1 as compared to the other two approaches which rely on the men of the pixel intensity.

Figure 5:
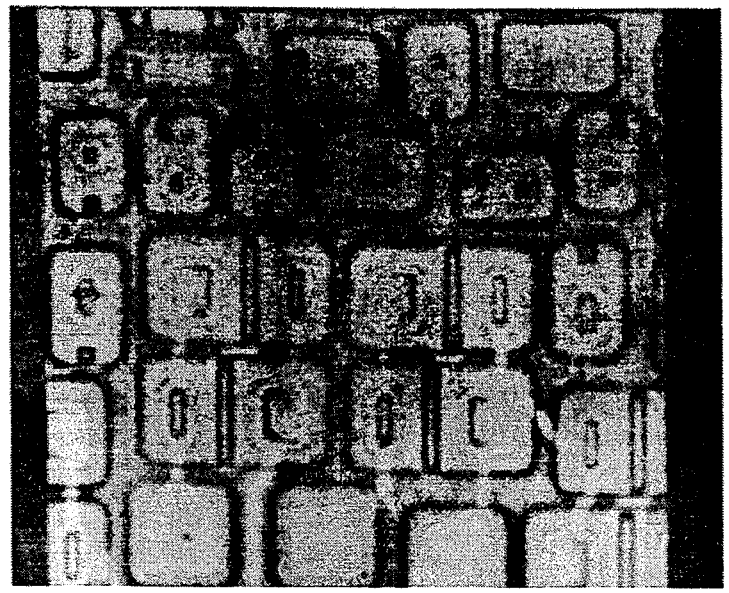
FIG. 5 shows the image of the chip of FIG. 3 after transformation of the pixel intensities.
Figure 6:
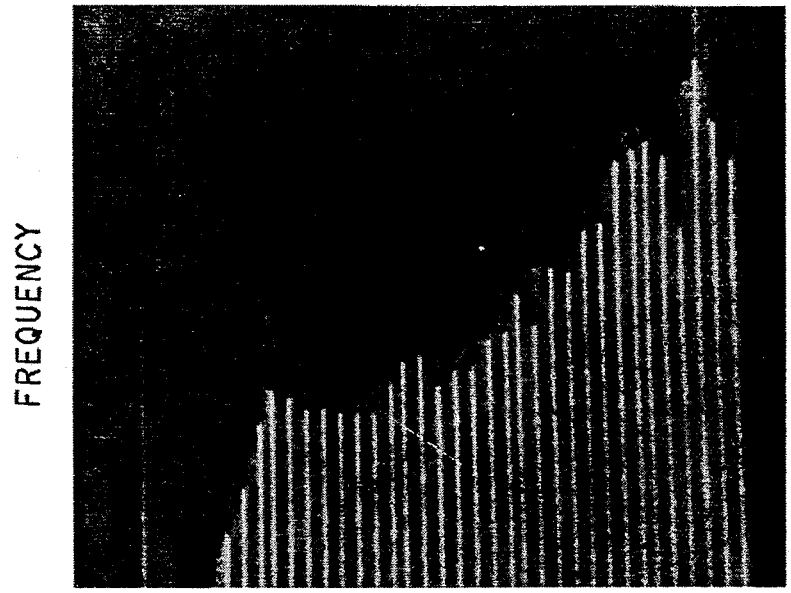
FIG. 6 is a histogram of the pixel intensities within the image of FIG. 5 after the pixel intensities have been normalized.

When establishing the threshold value t in accordance with the pixel intensity at a point just below the first non-zero peak of the histogram of FIG. 4, it is useful to expand or stretch the histogram in order to make the firs non-zero peak more prominent. This may be accomplished by first assigning an intensity value, equal to the mean pixel intensity, to those pixels within the image of FIG. 3 whose intensity exceeds the mean intensity. FIG. 5 shows the image of FIG. 3 after the above-described pixel intensity transformation has been made. Thereafter, the intensity of each of the pixels in the image of FIG. 5 is normalized (i.e., scaled) so the range of the pixel intensities is now 0–255. FIG. 6 shows the histogram of the image of FIG. 5 after the intensity of the pixels in the image has been normalized, and after the highest peak associated with the pixels which now have an intensity value equal to the mean intensity, has been discarded. AS may now be appreciated by comparison of FIGS. 4 and 6, the first non-zero peak in the histogram of FIG. 6 is more prominent, allowing the threshold value t to be more easily established.

Figure 7:
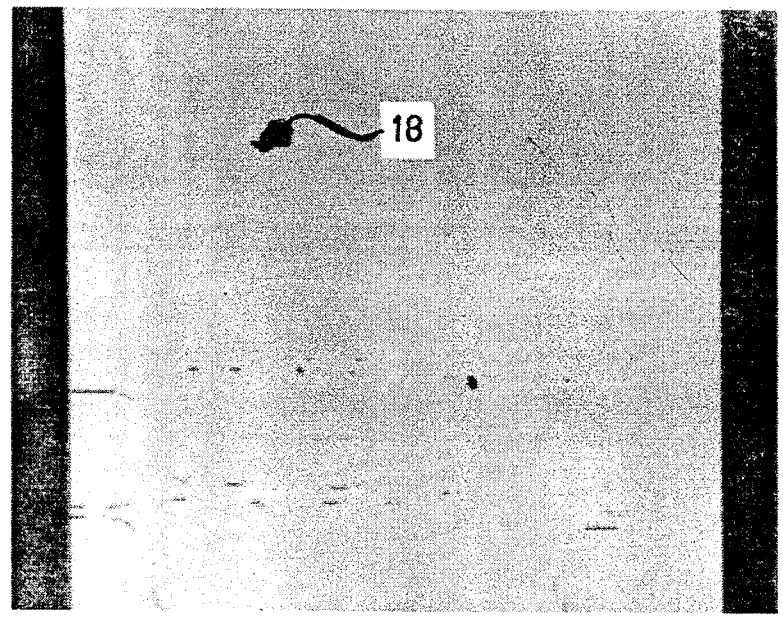
FIG. 7 shows the image of the chip of FIG. 5 after binarization.

Once the threshold intensity value t has been established during step 38 of FIG. 2, the image corresponding to the histogram of FIG. 6 (i.e., the normalized image of FIG. 5) is then binarized during step 40 of FIG. 2. Binarization of the image, whose true intensity is below the value t, to a zero gray level so the pixel appears black, whereas those pixels whose true intensity is above the value t are accorded a gray level of 255 so the pixels appear white. FIG. 7 shows the binarized image of the surface 15 of the chip 10 of FIG. 1 following step 40 of FIG. 2. As can be seen in FIG. 7, the only regions within the binarized image of the chip 10 which appear dark are the defect 18 and the features 16 (i.e., the tubs) which normally appear dark.

Following step 40 of FIG. 2, the image of FIG. 7 is further processed during step 42 to remove therefrom the features 16 (i.e., the tubs) which regularly appear dark in the image in order to isolate the dark area in FIG. 7 associated with the defect 18. Removal of the regularly occurring dark features 16 within the image of FIG. 7 can be accomplished during step 42 of FIG. 2 in several different ways. The simplest and most efficient method is to first repetitively erode (diminish) and then repetitively dilate (expand) all of the dark areas (i.e., the areas associated with the dark, regularly occurring features 16 and the defect 18) within the image of FIG. 7. Erosion and dilation of dark areas within the image of FIG. 7 is known in the art as a morphological "opening" operation.

Figure 8:
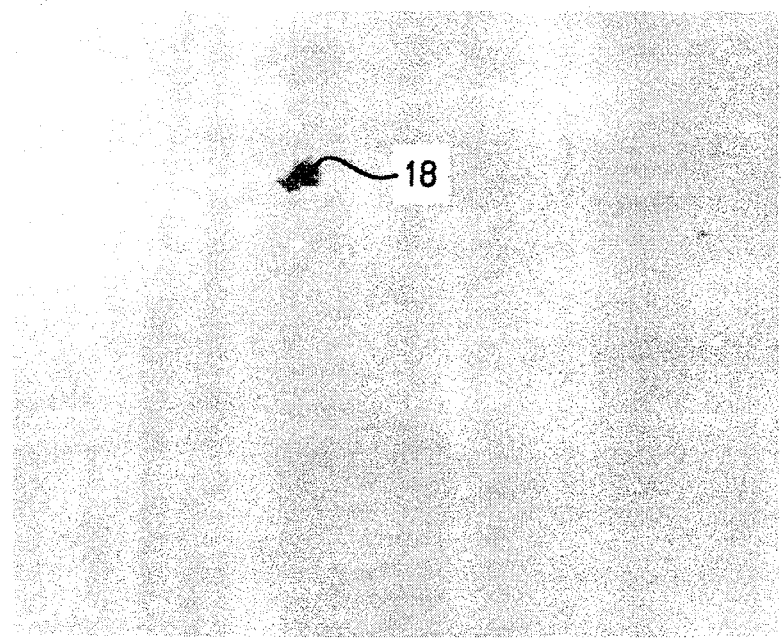
FIG. 8 shows the image of FIG. 7 after the dark areas therein have been eroded and dilated to isolate each dark area associated with each defect.

Erosion of the dark areas within the image of FIG. 7 is accomplished by causing those dark (i.e., black) pixels, within a ring one or two pixels wide, contiguous with the periphery of each of the dark features 16 and the defect 18, to now appear white. As a result, a portion of each dark feature and a portion of the defect 18 within the image of FIG. 7 are removed (i.e., shrunk), causing the features and the defect to appear smaller. The dark areas in the image of FIG. 7 are repeatedly dilated until those dark areas associated with the regularly occurring feature 16 in FIG. 3 are eliminated. The number of erosions is determined a priori by the linewidth of the features 16 in FIG. 3. Typically, only one or tow dilation operations are necessary before all of the dark areas associated with the regularly occurring features 16 are eliminated, as seen in FIG. 8. All that remains in FIG. 8 in the dark area associated with each defect 18.

After the dark areas within the image of FIG. 7 are repeatedly eroded, any dark areas which remain, as seen in FIG. 8, are then dilated the same number of times as the areas were eroded. Each dark area remaining within the image of FIG. 8 is successively dilated by causing those white pixels, within a ring one or two pixels wide circumscribing the periphery of the dark area, to now appear dark (i.e., black). In this way, the size of the defect 18 in FIG. 8, is increased after each dilation. Note that any of the dark areas in the image of FIG. 7 which had been removed (e.g., turned white) after the erosion operation do not reappear after dilation.

The reason why successive erosion of the dark areas within the image of FIG. 7 causes the regularly occurring dark features 16 to be removed is that, in practice, the regularly occurring dark features (i.e., the tubs) tend to be much narrower than the defect 18. Since the dark features 16, whose corresponding dark areas remain within the image of FIG. 3 following binarization thereof during step 40 of FIG. 2, tend to be much narrower than the defects 18, the dark areas corresponding to the features tends to disappear after only a few erosions, whereas the dark areas associated with the defect do not. Note that the size of the defect 18 in FIG. 8 is about the same as in FIG. 7. The reason why is that the defect 18 is substantially returned to its former size by the subsequent dilations performed after the erosion operations have been completed.

There are alternative approaches that may be employed during step 42 of FIG. 2 to remove the regularly occurring dark features 16 present in the image of FIG. 7. For example, during step 42 of FIG. 2, the intensity of the pixels within the image of FIG. 7 could be modified using a low pass filter (not shown) and then threshold in order to remove those pixels associated with the dark, regularly occurring features 16. However, in practice, the method of repetitively eroding and dilating the dark areas in the image of FIG. 7 in succession to isolate the dark area associated with the defect 18 was found to be more efficient.

Referring to FIG. 2, after step 42, the location and size of the defect 18 of FIG. 1 are established during step 44. The location and area of the defect 18 are determined from the location and size of the dark area within the image of FIG. 8. As may be appreciated, since all of the regularly occurring dark features 16 have already been eliminated from the image of FIG. 7 during step 42 of FIG. 2, the only dark area which remains within the image, as seen in FIG. 8, is associated with the defect 18. The location and size of the dark area in FIG. 8 can be determined from the location and number of dark (i.e., black) pixels within the image. When multiple dark areas are present following step 42 of FIG. 2, it becomes necessary to perform a connectivity analysis to determine how the areas are connected in order to determine the size and location of the individual defects 18.

The foregoing describes a technique for inspecting a surface 15 on an article 10, such as a semiconductor chip, without the need to match the pattern on the surface of the chip to that of a golden pattern to detect a defect 18. The present method effectively detects a defect 18 which, although small, has at least a slightly larger linewidth than the dark, regularly occurring features 16 (i.e., the tubs) on the surface 15 of the chip 10.

In addition to isolating each defect 18 of FIG. 1 which is larger than the linewidth of the regularly occurring features 16 of FIG. 1, the technique described above can be employed to isolate defects which are smaller than the linewidth of the features. In order to isolate the small defects 18, the level of illumination of the surface 15 within the field of view of the camera 30 of FIG. 1 must be substantially uniform so that the linewidths of the regularly occurring features 16 fall within a predetermined narrow band. Otherwise, isolation of the small defects 18 may prove extremely difficult.

Isolation of each defect 18 smaller than the linewidth of the regularly occurring features 16 on the surface 15 of the chip 10 of FIG. 1 is accomplished in much the same way the larger defects are isolated. First, the image of the surface 15 of the chip 10 is obtained, as per step 36 of FIG. 2. The image obtained during step 36 is then binarized, as per step 38 of FIG. 2. Thereafter, the dark areas within the binarized image are eroded and then dilated in the manner described with respect to step 42 of FIG. 2, not to remove the regularly occurring features 16, but to remove each small defect 18. The number of erosions, and the corresponding number of dilations, is determined a priori by the minimum linewidth of the features 16 in FIG. 3 such that each small defect 18 is eliminated while the regularly occurring features, and those large defects, if any, remain.

From the image containing only the regularly occurring features 16 and the large defects 18, the image obtained out by individually subtracting the intensity of each pixel within the image obtained during step 38 from each corresponding pixel within the image containing only the regularly occurring features 16 and the large defects 18. The resultant image obtained after subtraction is then inverted by causing each pixel which is dark to now appear white and vice verse. The now-inverted image contains only those defects 18 smaller than the linewidth of the regularly occurring features 16.

The techniques described above can be combined in the manner shown in flowchart form in FIG. 9 to obtain a composite image of those defects 18 which are both smaller and larger than the linewidth of the regularly occurring features 16. Referring to FIG. 9, the defects 18 larger than the linewidth of the features 16 are isolated (step 48) by performing the steps 36–42 of FIG. 2. Then, the image of the chip obtained during step 38 of FIG. 2 is also processed (step 48), as described above, to isolate the small defects 18. The image containing only the small defects 18 is logically ANDed (step 50) with the image containing only the large defects. The two images are logically ANDed by causing each pixel in the resultant containing only the small and the large defects 18 each appear white. For any other combination, the corresponding pixel in the resultant image obtained by ANDing the images containing only the large and the small defects 18 appears black.

Further, the regularly occurring features 16 can themselves be isolated from those defects 18 while are either smaller or larger. To isolate the regularly occurring features 16, the image containing the regularly occurring features and the large defects 18 is subtracted from the image containing only the larger defects. The resultant image obtained after subtraction is then inverted. The image which is obtained after inversion now contains only the regularly occurring features 16.

The foregoing described a technique for inspecting a surface by isolating, from the regularly occurring features 16, those defects 18 which are either smaller or larger than the linewidth of the features.

It is to be understood that the above-described embodiments are merely illustrative of the principles of the invention. Various modifications and changes may be made thereto by those skilled in the art which will embody the principles of the invention and fall within the spirit and scope thereof.

We claim:

1. A method for inspecting a patterned surface on an article, having at least one feature therein, to detect defects, if any, which are smaller than the linewidth of a dark-appearing feature on the surface, independently of any other pattern, the method comprising the steps of:

illuminating the surface of the article with light which is directed to strike the surface substantially normal to the plane thereof so that upon illumination of the surface, each defect, if any thereon, appears dark;

capturing the image of the surface of the article with an image-acquisition device whose optical axis is substantially normal to the axis of the surface;

binarizing the captured image to cause these areas within the image, which are associated with features in the patterned surface that have an intensity below a threshold value to appear dark, and those ares which are associated with regularly occurring features that have an intensity above the threshold value to appear bright;

processing the binarized image to produce a first image in which the feature on the surface and any defects larger than the linewidth of the feature, are isolated;

substracting the binarized image from the first image to yield a second image;

inverting the second image to yield a third image; and establishing the existence of a defect smaller than the linewidth of the feature on the surface by the presence of a dark area within the third image.

* * * * *